(12) United States Patent  
Gleason et al.

(10) Patent No.: US 9,393,056 B2  
(45) Date of Patent: Jul. 19, 2016

(54) PEDICLE SCREW EXTENSION SYSTEM

(71) Applicant: Spineology Inc., St. Paul, MN (US)

(72) Inventors: Joeseph Gleason, Eagan, MN (US); Steven Jacobson, Lake Elmo, MN (US)

(73) Assignee: Spineology Inc., St. Paul, MN (US)

( * ) Notice: Subject to any disclaimer, the term of this patent is extended or adjusted under 35 U.S.C. 154(b) by 0 days.

(21) Appl. No.: 14/942,553

(22) Filed: Nov. 16, 2015

(65) Prior Publication Data

US 2016/0066966 A1 Mar. 10, 2016

Related U.S. Application Data

(60) Continuation of application No. 14/599,681, filed on Jan. 19, 2015, now Pat. No. 9,186,188, which is a division of application No. 13/665,545, filed on Oct. 31, 2012, now Pat. No. 8,936,606.

(60) Provisional application No. 61/553,714, filed on Oct. 31, 2011.

(51) Int. Cl.
| | |
|---|---|
| *A61B 17/58* | (2006.01) |
| *A61B 17/60* | (2006.01) |
| *A61F 2/00* | (2006.01) |
| *A61B 17/70* | (2006.01) |
| *A61B 17/88* | (2006.01) |

(52) U.S. Cl.
CPC .......... *A61B 17/7076* (2013.01); *A61B 17/7082* (2013.01); *A61B 17/7088* (2013.01); *A61B 17/88* (2013.01); *A61B 17/7085* (2013.01); *A61B 17/7091* (2013.01); *Y10S 606/916* (2013.01)

(58) Field of Classification Search
None
See application file for complete search history.

(56) References Cited

U.S. PATENT DOCUMENTS

2006/0111730 A1* 5/2006 Hay ................... A61B 17/7088
606/104

* cited by examiner

*Primary Examiner* — Sameh Boles
(74) *Attorney, Agent, or Firm* — Skaar Ulbrich Macari, P.A.

(57) ABSTRACT

The pedicle screw extension system may include a removable cannulated extension provided to a pedicle screw tulip head. The cannulated extension may permit percutaneous implantation of pedicle screws followed by rod placement that may be guided by slots running along the length of the extension. The cannulation may allow for passage and attachment of secondary instruments, such as for example: a screw driving device, a rod measuring device, and a set screw driving device. The screw extension may also include secondary device attachment features allowing the rod to be pushed down in a screw tulip head and for extension removal as needed.

4 Claims, 4 Drawing Sheets

PEDICLE SCREW EXTENSION SYSTEM

PRIORITY

This application is a continuation of U.S. patent application Ser. No. 14/599,681, filed Jan. 19, 2015, which is a divisional of U.S. patent application Ser. No. 13/665,545, filed on Oct. 31, 2012, now U.S. Pat. No. 8,936,606, which claims the benefit of U.S. Provisional Application No. 61/553,714, filed on Oct. 31, 2011, wherein each of the preceding applications are hereby incorporated herein by reference in their entirety.

FIELD

The present invention generally relates to a pedicle screw extension system. More particularly, the present invention relates to a cannulated extension to a pedicle screw tulip head. The cannulated extension permits percutaneous implantation of pedicle screws followed by rod placement that is guided by slots running along the length of the extension.

BACKGROUND

Many systems exist for placing screws and other hardware into bone. However, there continues to be a need for a screw placement system that reliably and securely delivers the screws and facilitates screw removal when necessary. Further, there exists a need for an easy to use, reliable screw extension system that permits percutaneous implantation of pedicle screws.

SUMMARY

According to one aspect of the present invention, the pedicle screw extension system may include a removable cannulated extension provided to a pedicle screw tulip head. In one embodiment, the cannulated extension may permit percutaneous implantation of pedicle screws followed by rod placement that may be guided by slots running along the length of the extension. In an embodiment, the cannulation may allow for passage and attachment of secondary instruments, such as for example: a screw driving device, a rod measuring device, and a set screw driving device. In another embodiment, the screw extension may also provide secondary device attachment features allowing the rod to be pushed down in a screw tulip head and for extension removal as needed.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
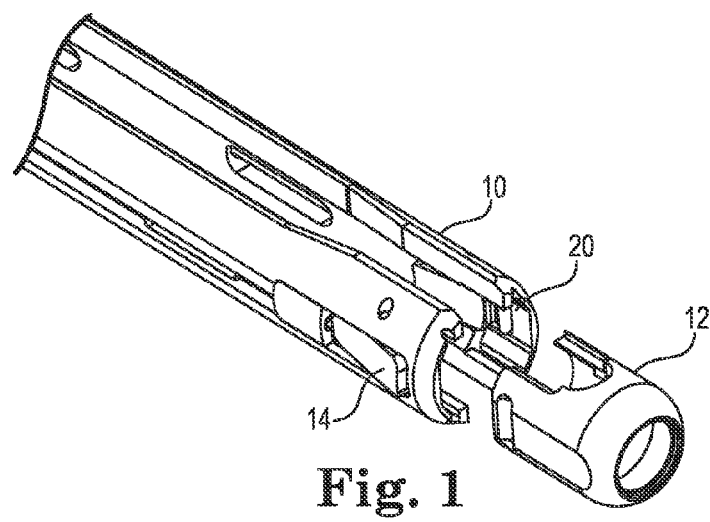
FIG. 1 is a perspective view of a portion of a pedicle screw extension system according to certain embodiments.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, combinations and alternatives falling within the spirit and scope of the invention as defined by the appended claims.

DETAILED DESCRIPTION

In the following descriptions, the present invention will be explained with reference to example embodiments thereof. However, these embodiments are not intended to limit the present invention to any specific example, embodiment, environment, applications or particular implementations described in these embodiments. Therefore, description of these embodiments is only for purpose of illustration rather than to limit the present invention. It should be appreciated that, in the following embodiments and the attached drawings, elements unrelated to the present invention are omitted from depiction; and dimensional relationships among individual elements in the attached drawings are illustrated only for ease of understanding, but not to limit the actual scale.

Figure 2:
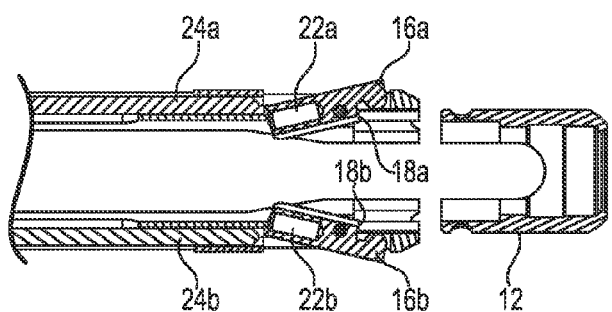
FIG. 2 is a cross-sectional view of a portion of a pedicle screw extension system according to certain embodiments.
Figure 3:
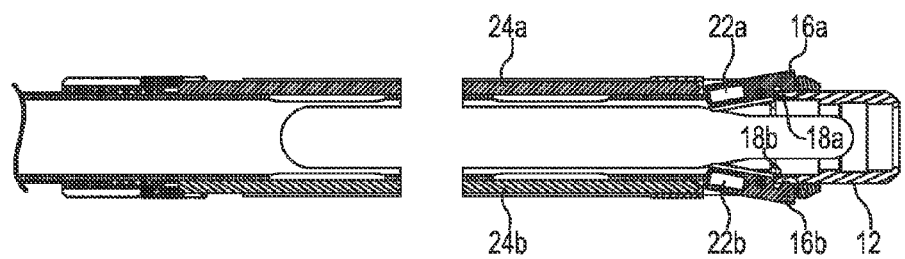
FIG. 3 is a cross-sectional view of a portion of a pedicle screw extension system according to certain embodiments.
Figure 4:
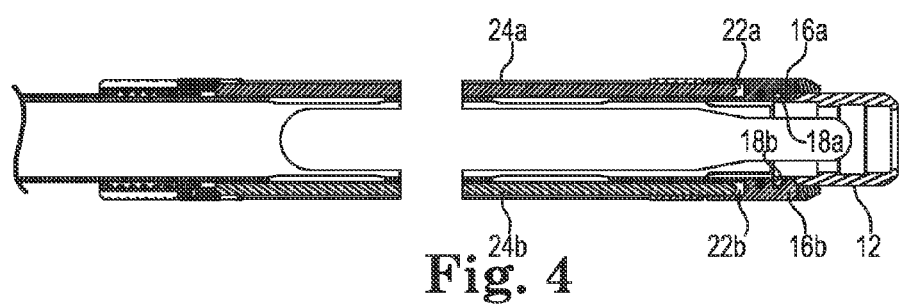
FIG. 4 is a cross-sectional view of a portion of a pedicle screw extension system according to certain embodiments.

In an embodiment as can be seen in FIGS. 1-4, the screw extension 10 may attach to and/or lock onto a screw tulip head 12 by a unique hinged capture locking mechanism 14. FIG. 2 depicts the locking mechanism 14 in an open position. FIG. 3 depicts the locking mechanism 14 in a partially closed position grasping a screw 12. FIG. 4 depicts the locking mechanism 14 in a fully closed position having the screw 12 fully secured. This hinged locking mechanism 14 pivots locally which provides for extremely strong holding power. In one embodiment, the locking mechanism 14 may be comprised of small distal hinged locking doors that may be constrained for maximum open and closed angular positions utilizing designed interferences to the door opening. According to one aspect, the locking mechanism 14 may float in its angular constrained range of motion. In an embodiment, the locking mechanism 14 may include radiused interference bars 16a and 16b on its distal end. The locking mechanism 14 may further include closing platforms 18a and 18b, adjacent to the interference bar, that may be timed to the spacing of mating geometries on a screw tulip head 12.

As shown in FIGS. 1-4, in one embodiment, a screw tulip head 12 may be loaded into a distal pocket 20 thus constraining lateral movement of extension arms. According to one aspect, as an implant/screw 12 is placed into a pocket 20 on the distal end of the extension 10, locking doors may be displaced to an open angular position as the implant slides past a radiused interference bar 16a or 16b of the locking door. In an embodiment, a proximal surface of a screw tulip head 12 may contact a closing platform 18a or 18b of the locking door such that the door closes as the tulip head 12 is seated in the final loaded position within the screw extension 10.

In yet another embodiment shown in FIGS. 1-4, the locking doors may include a cylindrical channels 22a and 22b perpendicular to an angular pivot point such that when the locking door is closed the cylindrical channel 22a or 22b may be oriented along the axis of the screw extension 10. According to one aspect, the screw extension 10 system may employ locking bars 24a and 24b that are driven along the axis of the screw extension 10 into the cylindrical channels 22a and 22b of the locking doors precluding any angular motion of the locking doors which then restricts linear motion of the screw tulip head 12, thus locking the screw/implant 12 onto the screw extension 10, much like a dead bolt style lock. In yet another embodiment, lock bars 24a and 24b may be withdrawn out of the lock doors allowing the lock doors to freely swing through their angular pathway. According to one embodiment, pulling a screw tulip head 12 out of a distal screw extension 10 pocket 20 may cause the radius lock bar 24a and 24b features to ramp out of a mating pocket on the screw tulip head 12, such that the tulip head 12 is freed for removal. Nearly no force is required to load or unload a screw tulip head 12.

Locking mechanism 14 may include a rounded detent which allows a screw head 12 to roll out in the unlocked state. Locking mechanism 14 may pivotally roll out of the locked position due to the linear motion of implant 12 removal. Cylindrical lock bars 24a and 24b may rest in cylindrical seats on locking mechanisms 14 giving holding strength. Lock bars 24a and 24b may be actuated by rotational movement of a turn knob and/or wheel 26. The lock knob 26 may be a rotary threaded device that drives the lock rods 24a and 24b linearly. The threads on the lock knob 26 produce linear motion from rotation.

Figure 5:
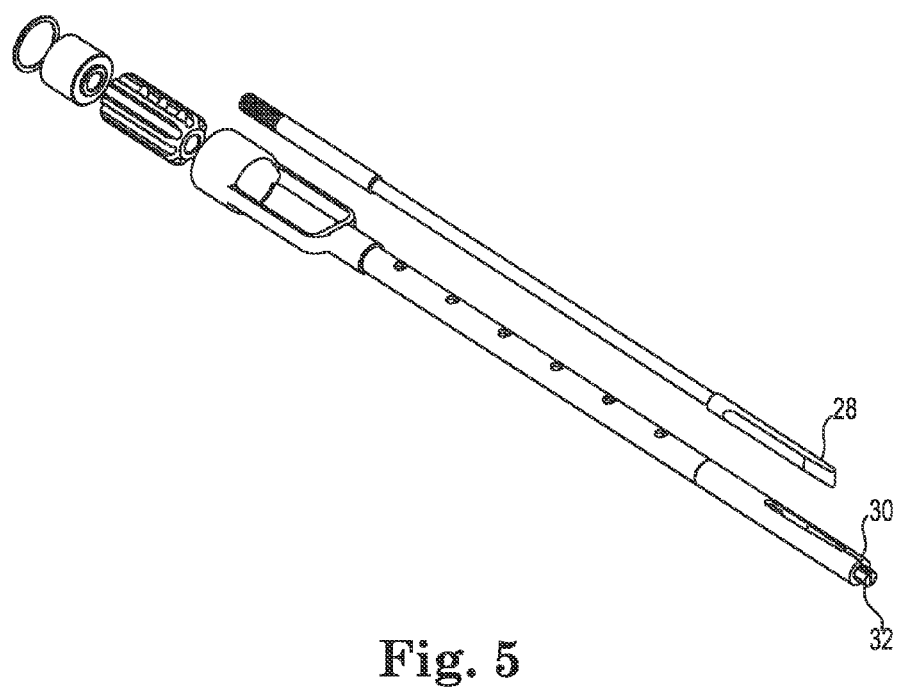
FIG. 5 is a perspective exploded view of a pedicle screw extension system according to certain embodiments.

As can be seen in FIG. 5, a rotating motion may drive a male wedge 28 linearly to open a stationary split female wedge 30 to mate with the male wedge 28 which drives the hex 32 apart causing interference between the hex 32 of the set screw placer and the hex of the screw resulting in extreme frictional holding force.

Figure 6:
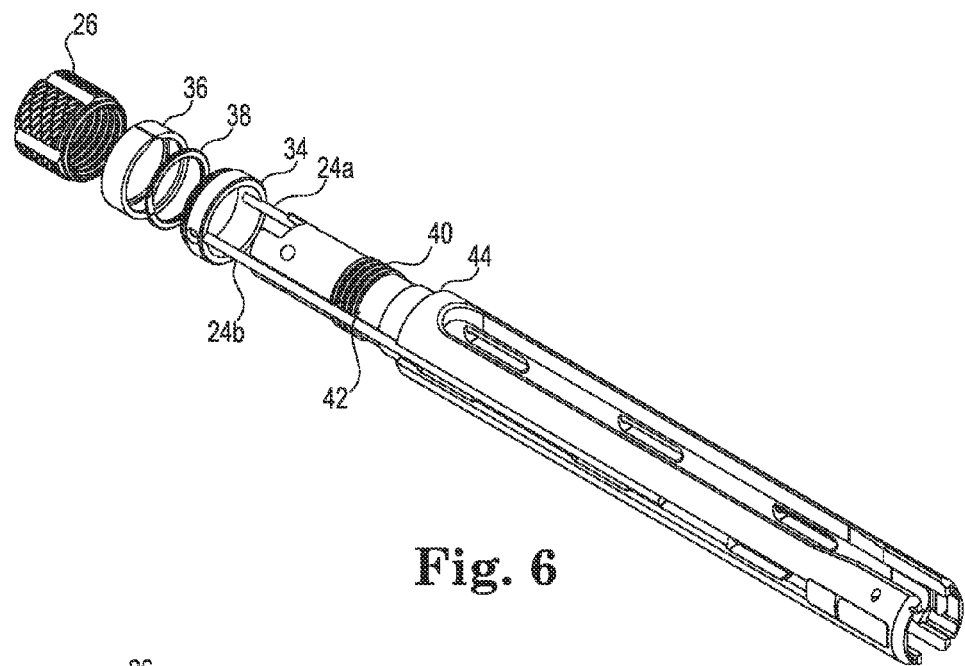
FIG. 6 is a perspective exploded view of a pedicle screw extension system according to certain embodiments.
Figure 7:
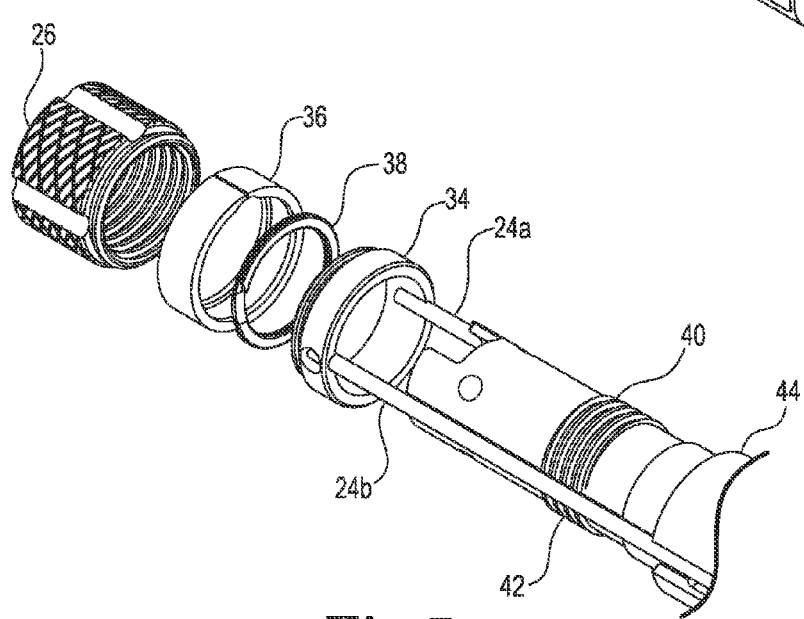
FIG. 7 is a perspective exploded view of a portion of a pedicle screw extension system according to certain embodiments.

According to an embodiment as can be seen in FIGS. 6-7, locking bars 24a and 24b may be coupled together by a cylindrical ring 34 concentric to the screw extension 10 which only moves in a linear motion along the axis of the screw extension 10. Lock rods 24a and 24b and rotating lock knob 26 may be coupled such that the rods 24a and 24b may be driven forward and backward. In one embodiment, the locking bar ring 34 may be driven linearly by a rotating threaded locking wheel and/or knob which may be coupled to a locking bar ring. The locking bar ring 34 may include an intermediary floating ring 36 having male groove protrusions which may engage female groove cuts in both the locking bar ring and locking wheel.

As shown in FIGS. 6-7, in one embodiment, a stop ring 38 may be nested between a locking wheel and a locking bar ring 34 and entrapped by a coupling ring. According to one aspect, the stop ring 38 may be a spiral wrapped ring or a split half moon ring pair. In an embodiment, the stop ring 38 may be positioned distally forward of a male thread 40 on the screw extension 10 providing a proximal stop 42. According to one aspect, a distal stop wall 44 may be designed into the screw extension 10. In one embodiment, clockwise lock wheel 26 rotation may drive the lock bars 24a and 24b distally into cylindrical lock door channels 22a and 22b until a stop wall 44 is reached. Counter clockwise lock wheel 26 rotation may withdraw lock bars 24a and 24b out of the door channels 22a and 22b until the stop ring 38 precludes proximal linear motion by abutting to the distal end of the male threads 40 on the screw extension 10. Extension 10 is elf contained and requires no secondary tools to load and unload screws 12.

According to one aspect, the screw extension 10 system may employ secondary devices for pushing a rod down the extension system and seating the rods into a screw tulip head 12 both internally and externally of the cannulated extension. Additional secondary devices may be used for removing the screw extension from the screw tulip head.

Figure 8:
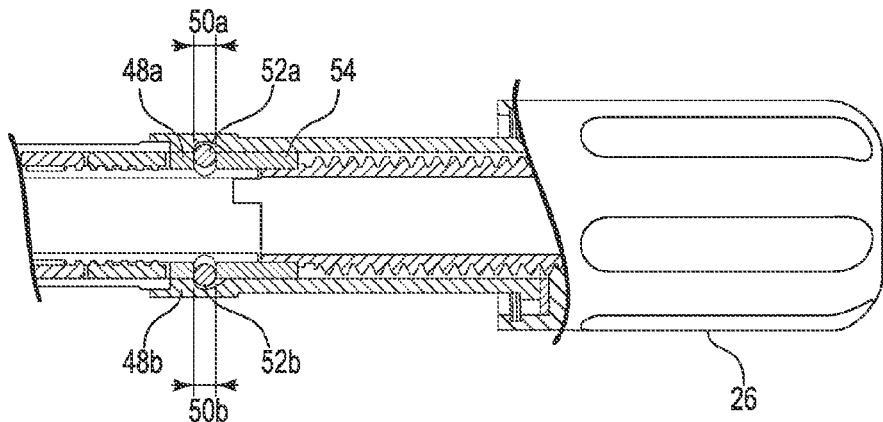
FIG. 8 is a cross-sectional view of a portion of a pedicle screw extension system according to certain embodiments.
Figure 9:
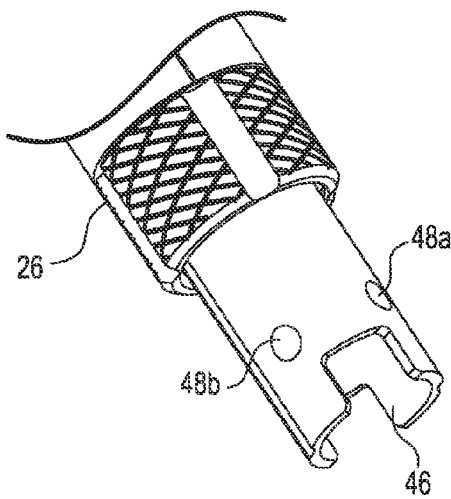
FIG. 9 is a perspective view of a portion of a pedicle screw extension system according to certain embodiments.
Figure 10:
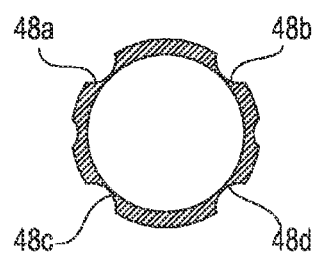
FIG. 10 is a cross-section end view of a portion of a pedicle screw extension system according to certain embodiments.

In one embodiment of the present invention, the screw extension 10 may include novel features on its proximal end as shown in FIGS. 8-10. According to one embodiment, the screw extension 10 may include a slot 46 configured for secondary device radial alignment with respect to the extension's 10 longitudinal axis. In yet another embodiment, the screw extension 10 may include spherical recessed cuts (dimples) 48a-d. In one embodiment, the screw extension 10 may include 4 dimples 48a-d. According to one aspect, the dimples 48a-d may provide engagement locations and bearing surfaces for interlocking secondary devices to the extension 10. Dimples 48a-d may be utilized to increase the force bearing contact surface with engaging spherical balls of a secondary device. The spherical recessed cuts 48a-d provide an increased surface area for bearing force versus a traditional 360 degree spherical groove.

As can be seen in FIGS. 8-10, according to one embodiment, secondary devices may utilize primary housings having radial cylinders 50a and 50b perpendicular to the axis of the screw extension 10 and/or housing and floating ball bearings 52a and 52b matched to the radial positions of the dimples 48a-d in the extension. A secondary housing 54 may contain a radial groove which when aligned with the cylinders 50a and 50b may allow the balls 52a and 52b to float out from the central cylinder. When misaligned, the balls 52a and 52b may be forced into the path of the central cylinder and then into the matching dimples 48a-d of the extension 10 such that the devices are locked together preventing radial and linear movement.

The present invention may be embodied in other specific forms without departing from the spirit or essential attributes thereof, and it is, therefore, desired that the present embodiment be considered in all respects as illustrative and not restrictive. Those skilled in the art may recognize other equivalents to the specific embodiment described herein which equivalents are intended to be encompassed by the claims attached hereto.

What is claimed is:

1. A pedicle screw extension system configured for percutaneous placement of a screw in a mammal, comprising:
   a locking bar; and
   an extension body including an actuator at its proximal end, the actuator configured to drive the locking bar linearly along a longitudinal axis of the extension body into a locking mechanism to engage the screw,
   wherein the locking mechanism comprises a locking door pivotally attached to the extension, and
   wherein the actuator is configured to drive the locking bar into a channel of a respective locking door to secure the doors closed around a head of the screw.

2. The system of claim 1, wherein the actuator is configured to translate rotational motion into linear motion to pull the locking bar linearly along a longitudinal axis of the extension body and out of a locking mechanism, thereby releasing the screw.

3. A pedicle screw extension device configured for percutaneous screw placement in a mammal, comprising:
- an extension body including a locking mechanism at a distal end of the extension body, the locking mechanism including a locking door pivotally attached to the extension body such that insertion of a screw head opens the door to allow for seating of the screw head in the extension; and
- an actuator provided to a proximal end of the extension body, wherein the actuator is configured to drive a locking bar into a cylindrical channel of the locking door to secure the in the extension.

4. The device claim 3, further comprising an actuator provided to the proximal end of the extension body, wherein the actuator is configured to be rotated to remove the locking bar from the locking door to allow the screw to be removed from the extension.

* * * * *